United States Patent
Dorn

(10) Patent No.: US 11,252,102 B2
(45) Date of Patent: Feb. 15, 2022

(54) EFFICIENT METHOD FOR ACCESSING IMAGE DATA STORED IN A CLOUD

(71) Applicant: Siemens Aktiengesellschaft, Munich (DE)

(72) Inventor: Karlheinz Dorn, Kalchreuth (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 1331 days.

(21) Appl. No.: 14/623,273

(22) Filed: Feb. 16, 2015

(65) Prior Publication Data
US 2015/0312168 A1    Oct. 29, 2015

(30) Foreign Application Priority Data
Apr. 24, 2014    (DE) .......................... 102014207726.5

(51) Int. Cl.
| | |
|---|---|
| *G16H 30/20* | (2018.01) |
| *G16H 10/60* | (2018.01) |
| *G16H 40/67* | (2018.01) |
| *H04L 29/08* | (2006.01) |
| *H04L 12/927* | (2013.01) |

(52) U.S. Cl.
CPC .......... *H04L 47/803* (2013.01); *G16H 10/60* (2018.01); *G16H 30/20* (2018.01); *G16H 40/67* (2018.01); *H04L 67/02* (2013.01); *H04L 67/1095* (2013.01)

(58) Field of Classification Search
CPC ..... H04L 67/1095; H04L 67/02; G16H 10/60; G16H 30/20; G16H 40/67; G06F 19/321; G06Q 50/24

USPC ......................................................... 709/203
See application file for complete search history.

(56) References Cited

U.S. PATENT DOCUMENTS

| | | | |
|---|---|---|---|
| 2002/0073429 A1* | 6/2002 | Beane | G06F 19/321 725/105 |
| 2009/0103789 A1* | 4/2009 | Danner | G16H 30/20 382/128 |
| 2011/0214041 A1 | 9/2011 | Nolte | |
| 2012/0084350 A1 | 4/2012 | Xie | |
| 2012/0254368 A1 | 10/2012 | Sasaki et al. | |

(Continued)

OTHER PUBLICATIONS

German Report of Examination dated Jan. 15, 2015 for corresponding DE Application No. 102014207276.5.

*Primary Examiner* — Emmanuel L Moise
*Assistant Examiner* — Xiang Yu
(74) *Attorney, Agent, or Firm* — Harness Dickey & Pierce, P.L.C.

(57) ABSTRACT

A device transmits a request to access image data stored in a cloud and then receives an access path to the image data. If the image data are in a first data format, the device reads the image data via the access path, converts them into the second data format, and stores the converted image data in the cloud. It also modifies the access path according to a modification rule and stores the modified access path in the cloud. If the image data are in the second data format, the device either always reads the image data in the second data format via the access path or checks whether a special instruction has been defined. On the basis of the special instruction, the device either reads the image data in the second data format via the access path or remodifies the access path using the modification rule.

17 Claims, 5 Drawing Sheets

(56) References Cited

U.S. PATENT DOCUMENTS

| | | |
|---|---|---|
| 2013/0036135 A1 | 2/2013 | Brockey et al. |
| 2014/0142984 A1* | 5/2014 | Wright .................. G06F 19/321 |
| | | 705/3 |
| 2014/0143298 A1* | 5/2014 | Klotzer ............... H04L 67/2823 |
| | | 709/203 |
| 2015/0134365 A1* | 5/2015 | Keefe .................... G16H 10/60 |
| | | 705/3 |

* cited by examiner

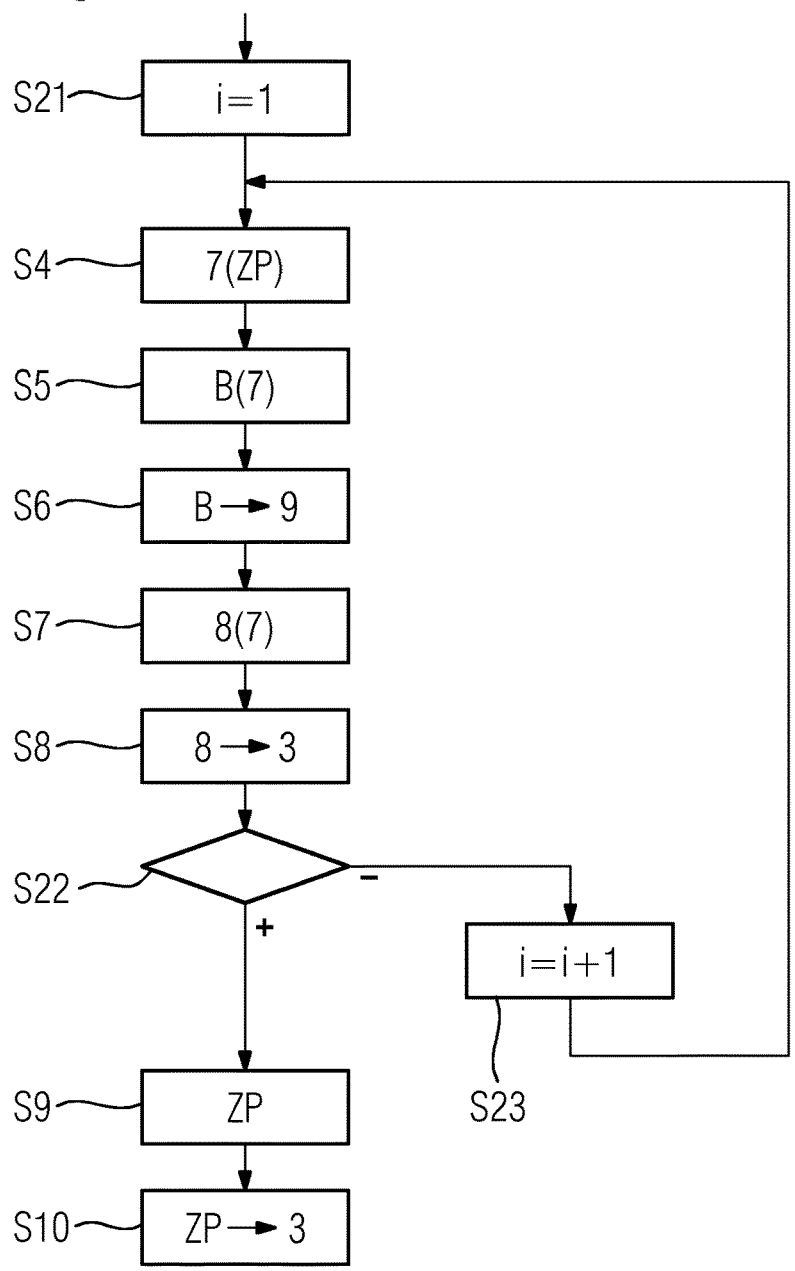

..../ namedcc/.../ name.dcm
..../ namedzc/.../ name.jpg

EFFICIENT METHOD FOR ACCESSING IMAGE DATA STORED IN A CLOUD

PRIORITY STATEMENT

The present application hereby claims priority under 35 U.S.C. § 119 to German patent application number DE 102014207726.5 filed Apr. 24, 2014, the entire contents of which are hereby incorporated herein by reference.

FIELD

At least one embodiment of the present invention generally relates to a method for accessing image data stored in a cloud, the method being carried out by a device.

At least one embodiment of the present invention also generally relates to machine-readable program code for a device, the program code having control instructions, the execution of which causes the device to carry out such an access method.

At least one embodiment of the present invention also relates to a device programmed with such program code.

BACKGROUND

The DICOM format is a standardized, manufacturer-neutral data format in medical data processing. In particular, two-dimensional or three-dimensional medical image data are often generated and stored in the DICOM format. The DICOM files define their own format which begins with a header area of variable length for meta data and ends with a data area for the pixel data which is likewise variable. This applies irrespective of the modality used to generate the images. Examples of such modalities are magnetic resonance systems, computer tomographs, C-arm X-ray systems, ultrasound scanners and more.

In the prior art, the generated images are stored more or less locally, for example via an intranet in a PACS (picture archiving and communication system) arranged inside a hospital. A protocol defined specifically for DICOM is often also used to transmit the data.

Recently, data are being transferred more and more to global systems, for example a so-called cloud. Such a transfer is also possible for DICOM data. However, in this case, the corresponding image data must be loaded from the cloud into a user's device each time the data are required by the user. The DICOM protocol itself and its use are not optimized for interaction with a cloud.

DICOM image data are often very comprehensive. The loading of such image data therefore considerably burdens the communication connection between the user's device and the cloud. This applies, in particular, when entire sequences of image data are retrieved from the cloud by the device and are output to the user via a display device, for example in an often repeated loop (so-called cine loop).

SUMMARY

At least one embodiment of the present invention provides possibilities which can be used to simplify access to the image data stored in the cloud in a simple and reliable manner.

At least one embodiment is directed to an access method. Dependent claims relate to advantageous refinements of the access method according to embodiments of the invention.

At least one embodiment of the invention provides an access method in which the device transmits a request to access the image data to the cloud, the device receives an access path to the image data from the cloud, the device uses the access path to check whether the image data are in a first data format or in a second data format, if the image data are in the first data format, the device
  reads the image data from the cloud via the access path,
  converts the image data inside the device into the second data format,
  stores the image data converted into the second data format in the cloud,
  modifies the access path according to a predetermined modification rule, with the result that the access path can be used to discern that the image data are stored in the cloud in the second data format, and
  stores the modified access path in the cloud, if the image data are in the second data format, the device
  either always reads the image data in the second data format from the cloud via the access path
  or checks whether a special instruction has been predefined therefor by a user and, on the basis of the special instruction,
    either reads the image data in the second data format from the cloud via the access path
    or remodifies the access path using the modification rule and reads the image data in the first data format from the cloud via the remodified access path.

At least one embodiment is directed to a machine-readable program code for a device, the program code having control instructions, the execution of which causes the device to carry out an access method according to at least one embodiment of the invention. The program code may be stored, in particular, on a storage medium.

At least one embodiment is directed to a device programmed with program code according to at least one embodiment of the invention.

BRIEF DESCRIPTION OF THE DRAWINGS

The above-described properties, features and advantages of this invention and the manner in which they are achieved become clearer and more easily understood in connection with the following description of the example embodiments which are explained in more detail in conjunction with the drawings, in which.

DETAILED DESCRIPTION OF THE EXAMPLE EMBODIMENTS

Figure 1:
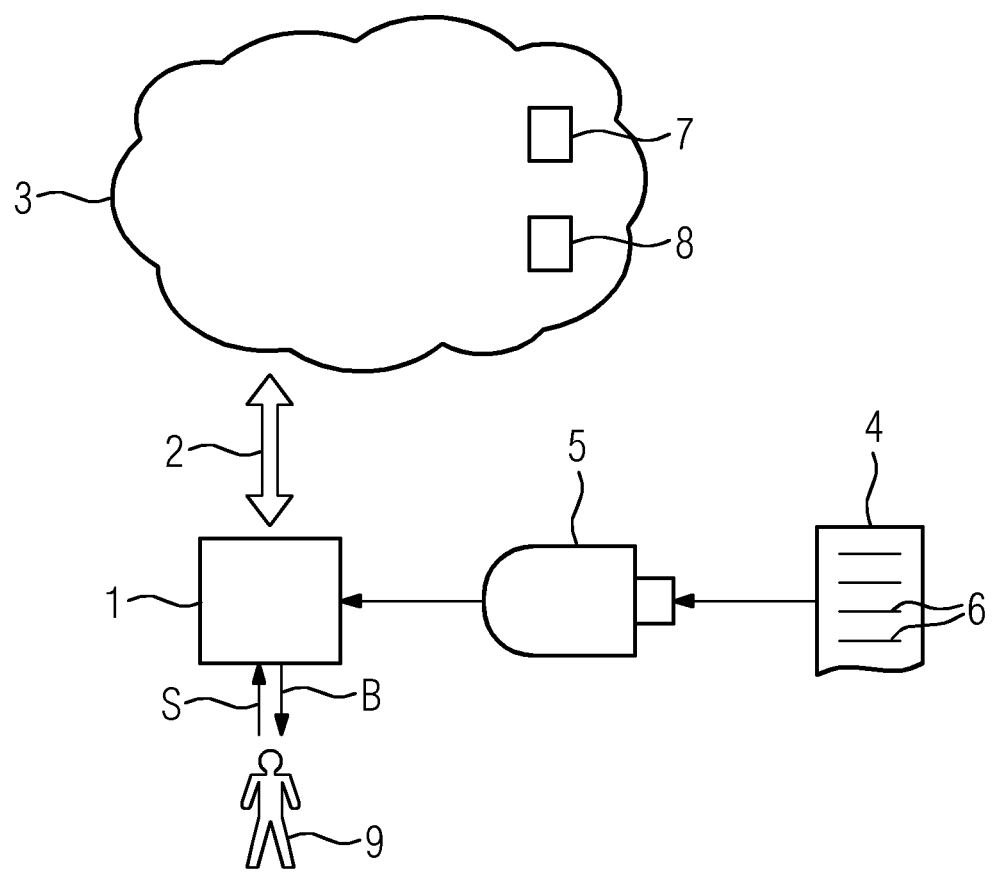
FIG. 1 schematically shows a device and a cloud,
FIG. 2 schematically shows a flowchart,
FIG. 3 schematically shows access paths,
FIG. 4 schematically shows a flowchart,
FIG. 5 schematically shows a flowchart,
FIG. 6 schematically shows access paths,
FIG. 7 schematically shows a flowchart, and
FIG. 8 schematically shows a flowchart.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the invention provides an access method in which
   the device transmits a request to access the image data to the cloud,
   the device receives an access path to the image data from the cloud,
   the device uses the access path to check whether the image data are in a first data format or in a second data format,
   if the image data are in the first data format, the device reads the image data from the cloud via the access path, converts the image data inside the device into the second data format,
      stores the image data converted into the second data format in the cloud,
      modifies the access path according to a predetermined modification rule, with the result that the access path can be used to discern that the image data are stored in the cloud in the second data format, and
      stores the modified access path in the cloud,
   if the image data are in the second data format, the device
      either always reads the image data in the second data format from the cloud via the access path
      or checks whether a special instruction has been predefined therefor by a user and, on the basis of the special instruction,
         either reads the image data in the second data format from the cloud via the access path or remodifies the access path using the modification rule and reads the image data in the first data format from the cloud via the remodified access path.

Although the image data are therefore reformatted by the procedure according to at least one embodiment of the invention, the local image resolution (length and width in pixels or length and width and depth in voxels) is retained. Further data which are relevant to interpreting the image data, for example the pixel or voxel size and the centering, are also retained. However, the coding of the image data is converted from the first data format into the second data format. This may—but need not—also be associated with a reduction in the data depth (for example only 8 bits instead of 16 bits previously). Depending on the data formats involved, the procedure according to the invention may achieve a data reduction by a factor of 10 or more, for example a data reduction by a factor of 20.

The access request may be, for example, a URL (universal resource locator). In response to the specification of the URL, the cloud may return another URL, for example, as the access path. However, other refinements are also possible.

When the image data are retrieved from the cloud for the first time using the procedure according to at least one embodiment of the invention (said data are therefore still and exclusively in the first data format), the execution of the procedure according to at least one embodiment of the invention is associated with a certain amount of additional effort. This is because the image data in the first data format need not only be read from the cloud. Rather, the image data must additionally also be converted into the second data format and stored in the cloud. However, the corresponding effort can generally be made in the background without the user noticing this. In contrast, for each further retrieval of the image data—irrespective of whether the data are retrieved using the same device or using another device which carries out the procedure according to at least one embodiment of the invention—the amount of communication effort is reduced by the procedure according to at least one embodiment of the invention.

The second data format may be lossy. However, this is generally of minor importance for a preliminary medical diagnosis. This is because the image data in the first data format, that is to say with their full information content, are also available if necessary, that is to say by specifying the corresponding special instruction.

On account of the change in the data format, it is also necessary to modify the access path. The modification generally comprises at least modifying the file type from an extension which characterizes the first data format to an extension which characterizes the second data format. However, the actual name of the access path is preferably retained on a 1:1 basis. As an alternative to retaining the name on a 1:1 basis, the modification of the access path may comprise changing a—and preferably only a single—folder in which the image data are stored. This last-mentioned refinement is advantageous, in particular, when the image data relating to a plurality of images form a group or sequence. This is because the corresponding images in the respective group or sequence can then be stored in the cloud in the first data format in a first folder and in the second data format in a second folder, the image data themselves—with the exception of the extension—having identical names and the folders in which the images are stored in the first data format and in the second data format in the cloud differing only in terms of one or two alphanumeric characters.

It is possible for the access method according to at least one embodiment of the invention to be carried out only by devices which have read access to the image data stored in the cloud. However, it is also possible for the access method according to at least one embodiment of the invention to be carried out by a device which stores the image data in the first data format in the cloud. Examples of such devices are computers which are connected to imaging modalities and accept the data acquired by the imaging modalities. In such a situation, it is therefore the case that, before transmitting a request to access the image data to the cloud, the device stores the image data in the first data format and an access path to the image data in the cloud. The device which stores the image data in the first data format in the cloud therefore itself also simultaneously ensures that the image data are also stored in the second data format in the cloud.

The original image data, that is to say the image data stored in the first data format, must generally be retained. It is possible for this storage to be effected in the cloud. Alternatively, it is possible for this storage to be effected outside the cloud. In the last-mentioned case, if the device stores the image data converted into the second data format and the modified access path in the cloud, it is possible for the device to read the image data stored by the device in the cloud in the second data format from the cloud, to check the image data read from the cloud in the second data format for identity with the image data previously converted by the device, in the event of identity, to delete the image data stored in the first data format in the cloud, and in the event of a lack of identity, to carry out an error response.

The error response may involve, for example, making another attempt to store the image data in the second data format in the cloud, that is to say repeating the procedure explained above. Alternatively or additionally, it is possible to output an error message to the user.

Deleting the image data stored in the first data format may result, for example, in personal data which are present in the first data format in the image data no longer being included in the image data stored in the second data format.

In one example refinement, the access method is carried out in a manner embedded in a web browser. This provides the following advantage:

If the image data are already in the second data format—this also applies when the image data have been stored in the cloud immediately beforehand using this device—the image data are buffered in a temporary buffer memory reserved for the web browser in the device when said data are being read from the cloud. This is general practice in the case of web browsers. If the image data are intended to be repeatedly output to a user in such a case, for example using a display device, the image data are therefore read from the cloud in the first data format the very first time they are read, that is to say when they are only in the first data format, and are stored in the cloud in the second data format. When the data are read for the second time, that is to say when they are already in the second data format, the image data are read from the cloud in the second data format and are buffered in the temporary buffer memory of the web browser. For each further output to the user, there is no need for any access whatsoever by the web browser via the data network in such a case. This is because the image data in the second data format have already been stored in the temporary buffer memory of the web browser in this case. This is particularly advantageous if—as generally customary—a fee needs to be paid to use the cloud. This is because the user of the device must access the cloud a maximum of twice in this case. From the third access on, the image data are stored in the temporary buffer memory of the web browser.

The data formats can be determined as required. The first data format may be the DICOM format, in particular. The second data format may be the JPEG format or the PNG format, for example. All three data formats are generally known to experts.

At least one embodiment is directed to a machine-readable program code for a device, the program code having control instructions, the execution of which causes the device to carry out an access method according to at least one embodiment of the invention. The program code may be stored, in particular, on a storage medium.

At least one embodiment is directed to a device programmed with program code according to at least one embodiment of the invention.

According to FIG. 1, a device 1 is connected to a cloud 3 via the Internet 2. The device 1 may be, for example, a tablet, a PC, a smartphone etc. The device 1 may also be an imaging medical modality or may be connected to such a modality. The device 1 is programmed with a machine-readable program code 4. The machine-readable program code 4 may be supplied to the device 1 in any desired manner in principle. In particular, the machine-readable program code 4 may be stored on a storage medium 5 according to the illustration in FIG. 1. The storage medium 5 in turn may likewise be of any desired nature. The illustration in FIG. 1, in which the storage medium 5 is illustrated as a USB memory stick, is purely exemplary. The machine-readable program code 4 has control instructions 6 which can be executed by the device 1. The execution of the control instructions 6 causes the device 1 to carry out a method for accessing image data 7, 8 stored in the cloud 3. The access method is explained in more detail below in conjunction with the further FIGS.

Figure 2:
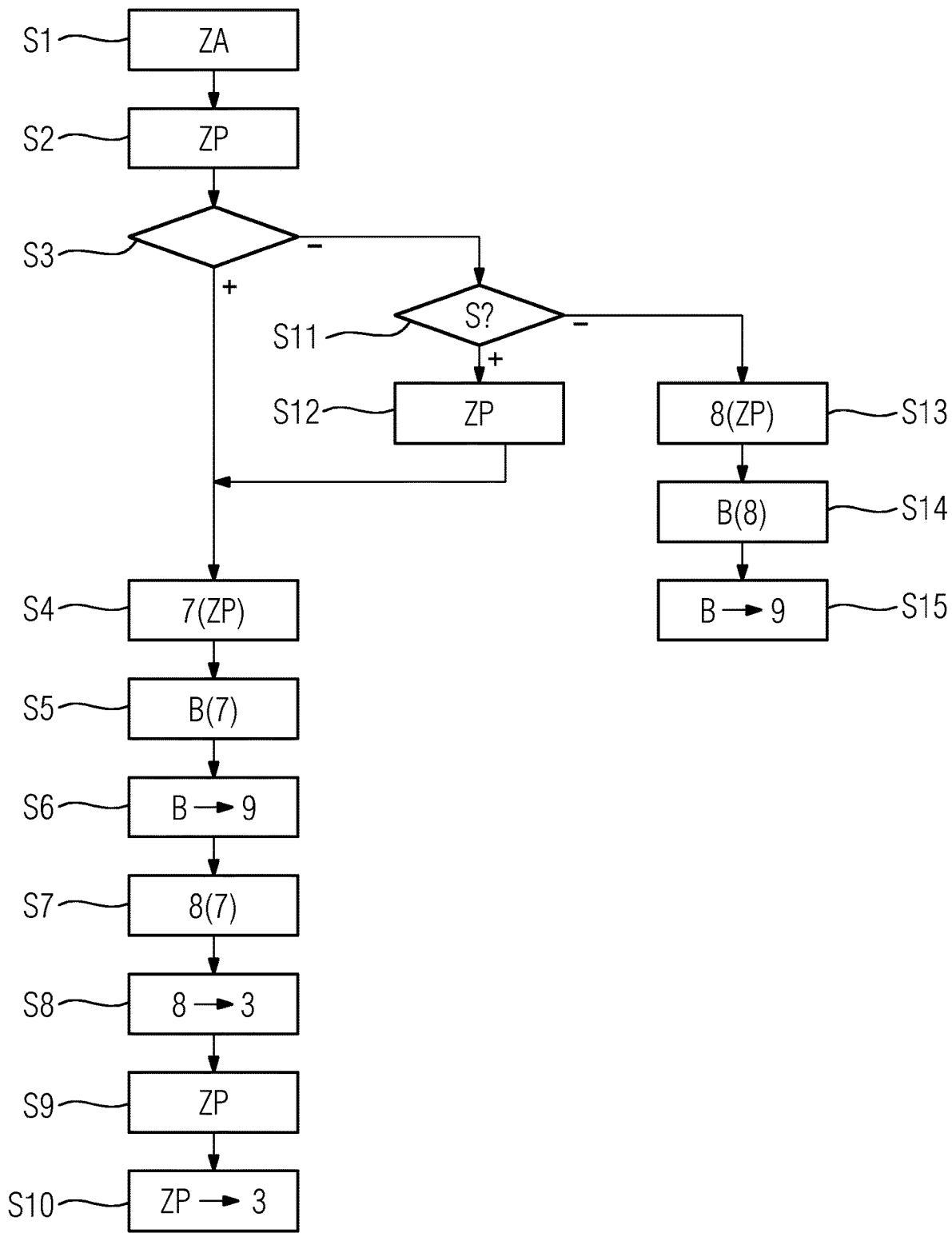

According to FIG. 2, the device 1 transmits a request ZA to access the image data 7, 8 to the cloud 3 in a step S1 within the scope of the access method according to an embodiment of the invention. The access request ZA may be a URL, for example. It may specify, for example, a person, a date and a region of the person's body.

In a step S2, the device 1 receives an access path ZP to the image data 7, 8 from the cloud 3. The access path ZP contains (inter alia) the information relating to whether the image data 7, 8 are in a first data format (image data 7) or in a second data format (image data 8). The access path ZP may be a URL, for example.

In a step S3, the device 1 uses the access path ZP to check whether the image data 7, 8 are in the first data format or in the second data format. Further measures are taken depending on the check in step S3.

For reasons of better clarity, an embodiment of the present invention is explained below assuming that the first data format is the DICOM format and the second data format is the JPEG format. This configuration is a frequent application. If the text below therefore refers to the DICOM format, the first data format in its generality is always intended, not specifically the DICOM format. In a similar manner, if the text below refers to the JPEG format, the second data format in its generality is always intended, not specifically the JPEG format. In particular, the second data format could alternatively be the PNG format, for example.

If the image data 7, 8 are in the DICOM format, the device 1 changes to steps S4 to S10. In step S4, the device 1 reads the image data 7 from the cloud 3 via the access path ZP. Reading takes place in the DICOM format.

In step S5, the device 1 carries out so-called rendering of the image data 7 which have been read, that is to say determines an associated image B. In step S6, the device 1 outputs the rendered image B to a user 9 of the device 1. As far as the access method according to the invention is concerned, steps S5 and S6 are not absolutely necessary as such. However, they are usually present.

In step S7, the device 1 converts the image data 7 inside the device 1 into the JPEG format. The device 1 therefore generates the image data 8 (JPEG format). In step S8, the device 1 stores the image data 8 in the cloud 3. Storage is effected at that address which is accessed using the access request ZA.

In step S9, the device 1 modifies the access path ZP. The modification is carried out according to a predetermined modification rule, specifically in such a manner that the modified access path ZP can be used to discern that the image data 8 are stored in the cloud 3 in the JPEG format. In step S10, the device 1 stores the modified access path ZP in the cloud 3.

The image data 7 in the DICOM format consist of a header and the actual useful data. The image data 8 in the JPEG format likewise consist of a header and the actual useful data. The header of the DICOM image data 7 contains, inter alia, data relating to the image B as such, for example its length, its width, its depth in the case of a three-dimensional image B, its pixel or voxel size, its centering and so on. The header also contains, for example, data relating to the person from whom the image data 7 originate, that is to say the person who is represented in the image data 7, when and where the image data were acquired and so on (personal medical data). In order to convert the image data 7 into the image data 8, the device 1 indeed uses the data relating to the image B as such. The JPEG image data 8 therefore show an image B which has, for example, the same length and the same width, possibly also the same depth, and the same pixel or voxel size as the DICOM image data 7. The other data, that is to say the personal medical data, are preferably not transferred to the JPEG image data 8.

In contrast, if the image data 7, 8 are in the JPEG format, the device 1 changes to a step S11. In step S11, the device 1 checks whether a special instruction S has been predefined therefor by the user 9. If this is the case, the device 1—irrespective of whether or not the image data 7, 8 are in the JPEG format in the cloud 3—always reads the DICOM image data 7 from the cloud 3. The device 1 therefore changes to a step S12. In step S12, the device 1 uses the modification rule to remodify the access path ZP. The device 1 therefore determines, in step S12, that access path ZP which can be used to access the DICOM image data 7. The device 1 then reads the image data 7 from the cloud 3 via the remodified access path ZP. This can be carried out in the simplest manner by virtue of the device 1 changing to step S4 starting from step S12 according to the illustration in FIG. 2.

In contrast, if the special instruction S has not been predefined for the device 1 by the user 9, the device 1 changes to steps S13 to S15. In step S13, the device 1 reads the JPEG image data 8 from the cloud 3 via the access path ZP. In step S14, in a similar manner to step S5, the device 1 carries out so-called rendering of the image data 8 which have been read, that is to say determines an associated image B. In step S15, the device 1 outputs the rendered image B to the user 9 of the device 1. As far as the access method according to the invention is concerned, steps S14 and S15 are not absolutely necessary as such in a similar manner to steps S5 and S6. However, they are usually present.

Alternatively, it is possible to dispense with steps S11 and S12. In this case, after the check in step S3, the device 1 possibly changes directly to step S13.

FIG. 3 shows two access paths ZP by way of example. The top of FIG. 3 illustrates an access path ZP which is transmitted as part of step S2 when the access request ZA in step S1 is a request for an individual image B and the image data 7 are in the DICOM format. The bottom of FIG. 3 illustrates the corresponding access path ZP which is transmitted as part of step S2 when the access request ZA in step S1 is a request for an individual image B and the image data 7 are in the JPEG format. The access paths ZP are clearly largely identical. They differ only in the extension used for the data format, namely DCM for the DICOM format and JPG for the JPEG format. It can therefore be readily discerned from FIG. 3 that the device 1 must only check the extension as part of step S3, must only modify the extension from DCM to JPG as part of step S9 and must only modify the extension from JPG to DCM as part of step S12. Further changes are not required, in principle, if individual image data 7, 8 are requested.

Annexes 1 and 2 illustrate the specific access paths ZP in detail in a purely exemplary manner. The access paths ZP illustrated in annexes 1 and 2 are drafted in the XML format. Annex 1 shows the access path ZP to the DICOM image data 7, and annex 2 shows the access path ZP to the corresponding JPEG image data 8.

It is possible for the image data 7, 8 to comprise not only an individual image B but rather a group of images B. If the image data 7, 8 comprise a group of images B, it is possible, in principle, to carry out the procedure according to FIG. 2 in unchanged form for each individual image B. However, the procedure from FIG. 2 is preferably used in slightly modified form. This is explained in more detail below in conjunction with FIGS. 4 to 6.

According to FIG. 4, the sequence of steps S4 to S10 is first of all supplemented with steps S21 to S23. In step S21, the device 1 sets an index i to an initial value (for example to the value 1 according to the illustration in FIG. 4). In step S22, the device 1 checks whether the index i has reached its final value. Depending on the result of the check in step S22, the device 1 changes either to step S9 or to step S23. In step S23, the device 1 increases the value of the index i by 1. According to FIG. 5, the sequence of steps S13 to S15 is also supplemented with steps S26 to S28. Steps S26 to S28 correspond, in terms of content, to steps S21 to S23, with the result that reference can be made to the relevant statements.

Figure 6:
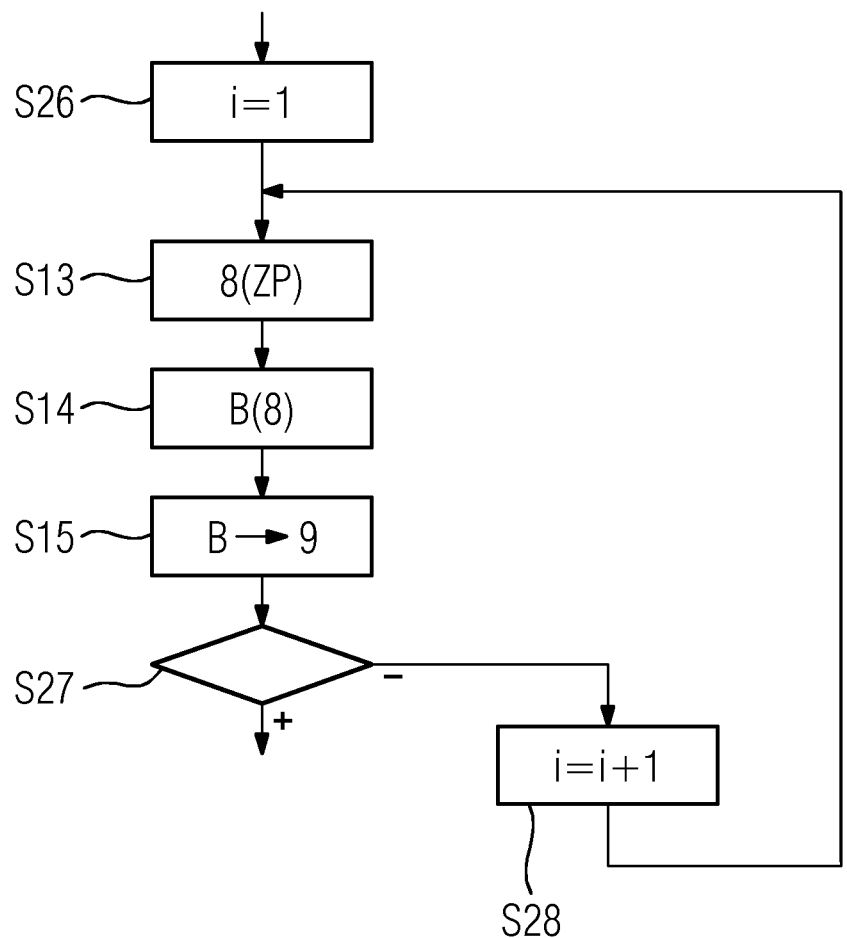

Based on the modification according to FIGS. 4 and 5, FIG. 6 shows two access paths ZP by way of example. The top of FIG. 6 illustrates an access path ZP which is transmitted as part of step S2 when the access request ZA in step S1 is a request for a plurality of images B and the image data 7 are in the DICOM format. The bottom of FIG. 6 illustrates the corresponding access path ZP which is transmitted as part of step S2 when the access request ZA in step S1 is a request for a plurality of images B and the image data 8 are in the JPEG format. The access paths ZP are clearly largely identical. They differ, on the one hand, in the extension used for the data format, namely DCM for the DICOM format and JPG for the JPEG format. They differ, on the other hand, in the name of a folder in which the image data 7 and 8 relating to the individual images B are stored in the cloud 3. Only these two changes preferably exist. The names of the two folders preferably also differ only in terms of one or two alphanumeric characters. For example, the name of the two folders may contain the letter sequence "DCC" or "DZC" depending on which data format is involved and may otherwise be identical.

In a similar manner to FIG. 3, it can also be readily discerned from FIG. 6 what check must be carried out by the device 1 as part of step S3 and what changes must be carried out by the device 1 as part of step S9 and step S12.

Annexes 3 and 4 illustrate the specific access paths ZP in detail purely by way of example for the case described last. The access paths ZP illustrated in annexes 3 and 4 are drafted in the XML format. Annex 3 shows the access path ZP to the DICOM image data 7, and annex 4 shows the access path ZP to the corresponding JPEG image data 8. Annexes 5 and 6 also illustrate, in XML format, the instruction sequences needed to sequentially retrieve the individual images B of the DICOM image data 7 (annex 5) and of the JPEG image data 8 (annex 6). Annex 7 shows, in HTML 5 and JavaScript, a possible instruction sequence which can be used to sequentially read the individual images of the DICOM image data 7 in succession from the cloud 3. Annex 8 shows, in HTML 5 and JavaScript, a possible instruction sequence which can be used to generate the JPEG images 8 and store them in the cloud 3.

As already mentioned, the device 1 may be, for example, an imaging medical modality or may be connected to such a modality. In this case in particular—but not only in this case in principle—it is possible to configure the access method according to an embodiment of the invention in the manner explained in more detail below in conjunction with FIG. 7.

Figure 7:
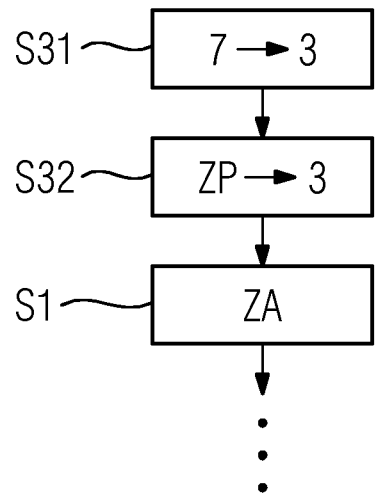

According to FIG. 7, steps S31 and S32 are arranged upstream of step S1 from FIG. 2. In step S31, the device 1 stores the image data 7 in the DICOM format in the cloud 3 (upload). In step S32, the device 1 also stores the associated access path ZP to the image data 7 which have just been stored in the cloud 3. Storage is effected at that address which is accessed using the access request ZA. On account of the fact that steps S31 and S32 are carried out before step S1, the DICOM image data 7 and the access path ZP are stored before a request ZA to access the image data 7 is transmitted to the cloud 3.

In a similar manner to the configuration according to FIG. 2, the configuration according to FIG. 7 is possible both with respect to an individual image B and with respect to a group of images B.

Figure 8:
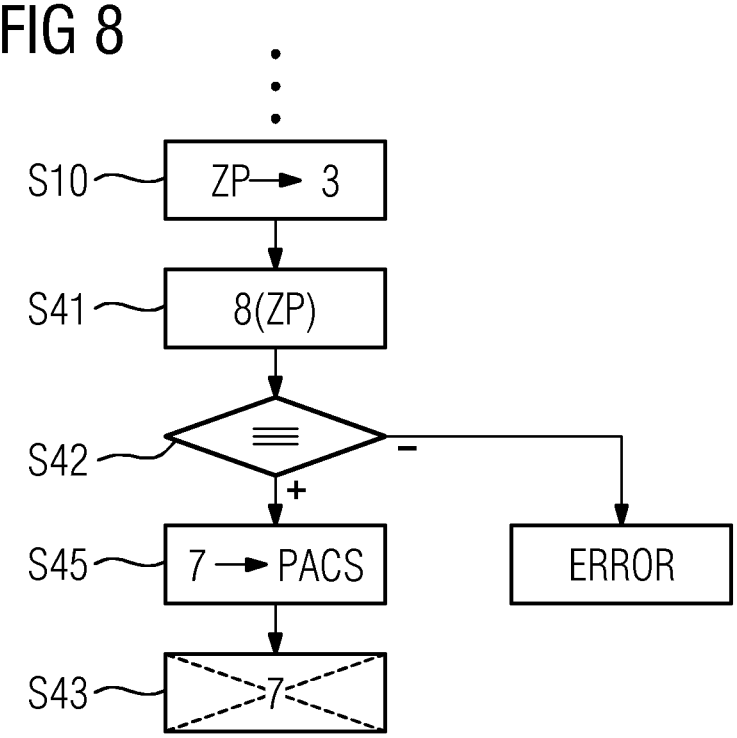

Alternatively or additionally to the configuration according to FIG. 7, it is possible to configure the access method according to FIG. 8. FIG. 8 shows an addition to steps S4 to S10 from FIG. 2. However, the addition could also be readily implemented if the access method is configured according to FIGS. 4 and 5. The configuration according to FIG. 8 is also preferably combined with the procedure from FIG. 7. However, it can also be implemented independently of this procedure. Within the scope of the configuration according to FIG. 8, the device 1 is preferably in the form of an imaging medical modality or is connected to such a modality. In principle, however, the device 1 can have any desired design.

According to FIG. 8, additional steps S41 to S44 are carried out after steps S4 to S10. In step S41, in a similar manner to step S13, the device 1 reads the JPEG image data 8 stored in the cloud 3 from the cloud 3. In step S41, the device 1 therefore reads precisely those JPEG image data 8 from the cloud 3 which were previously stored in the cloud 3 by the device 1. In step S42, the device 1 checks the JPEG image data 8 which have been read with the JPEG image data 8 generated in step S7 for identity. The device 1 therefore checks whether the JPEG image data 8 have been properly stored in the cloud 3. If this is the case, the device 1 deletes the corresponding DICOM image data 7 stored in the cloud 3 in step S43. After the DICOM image data 7 have been deleted, only the JPEG image data 8 are therefore still present in the cloud 3. Otherwise, the device 1 carries out an error response in step S44. The error response may involve, for example, carrying out a further attempt to write to the cloud 3. Alternatively, an error message can be output to the user 9.

The DICOM image data 7 are preferably deleted only when the DICOM image data 7 have been previously permanently stored elsewhere. According to FIG. 8, a step S45 is therefore preferably additionally present, in which such storage is effected. This storage can alternatively be effected in the cloud 3 or outside the cloud 3, for example in a PACS.

It is possible to move computing operations to the cloud 3. However, within the scope of the access method according to an embodiment of the invention, the cloud 3 is preferably used solely as a memory. This procedure additionally makes it possible to carry out an auto zoom and/or a zoom/pan, in particular, in a simple manner.

The access method according to an embodiment of the invention may be in the form of an independent application. However, the method is preferably carried out in a manner embedded in a web browser. This procedure is advantageous, in particular, when the JPEG image data 8 relating to a group of images B are sequentially and iteratively (that is to say in a repeatedly executed loop) retrieved from the cloud 3 and output to the user 9.

It is also possible to combine the reading of the image data 7, 8 from the cloud 3 with one another. For example, if the JPEG image data 8 relating to a group of images B are sequentially and iteratively retrieved from the cloud 3 and output to the user 9, the playback can be stopped by the user 9, with the result that, after stopping, the user 9 is given the opportunity to scroll through the images B. If the user 9 selects a particular image B or a particular subgroup of images B, the DICOM image data 7 relating to the selected image(s) B are retrieved and output to the user 9.

The duality of the image data 7, 8, that is to say the storage under virtually identical names and access paths ZP, makes it possible to manage mutually corresponding DICOM image data 7 and JPEG image data 8 in a simple and failsafe manner.

In summary, at least one embodiment of the present invention therefore relates to the following substantive matter:

A device 1 transmits a request ZA to access image data 7, 8 stored in a cloud 3 to the cloud 3 and then receives an access path ZP to the image data 7, 8 from the cloud 3. The device 1 uses the access path ZP to check the data format of the image data 7, 8. If the image data 7, 8 are in a first data format, the device 1 reads the image data 7 from the cloud 3 via the access path ZP, converts them inside the device 1 into the second data format, and stores the converted image data 8 in the cloud 3. It also modifies the access path ZP according to a modification rule, with the result that the access path ZP can be used to discern that the image data 8 are stored in the cloud 3 in the second data format, and stores the modified access path ZP in the cloud 3. If the image data 8 are in the second data format, the device 1 either always reads the image data 8 in the second data format from the cloud 3 via the access path ZP or checks whether a special instruction S has been predefined therefor by a user 9. In the case mentioned last, on the basis of the special instruction S, the device 1 either reads the image data 8 in the second data format from the cloud 3 via the access path ZP or remodifies the access path ZP using the modification rule and reads the image data 7 in the first data format from the cloud 3 via the remodified access path ZP.

Although the invention has been described and illustrated more specifically in detail by way of the example embodiment, the invention is not restricted by the disclosed examples and other variations can be derived therefrom by the person skilled in the art, without departing from the scope of protection of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

---

Annex 1

```
<Context>
<PartitionKey xmlns =
"http://schemas.datacontract.org/2004/07/Microsoft.Samples.Wi
ndowsPhoneCloud.StorageClient"> GER</PartitionKey>
<RowKey xmlns =
"http://schemas.datacontract.org/2004/07/Microsoft.Samples.Wi
ndowsPhoneCloud.StorageClient">13acb1e8-ca04-4527-af73-
4f6ba492bb4d</RowKey>
<Timestamp xmlns =
"http://schemas.datacontract.org/2004/07/Microsoft.Samples.Wi
ndowsPhoneCloud.StorageClient">2012-02-
21T10:27:07.6956173Z</Timestamp>
<ARegion>Head</ARegion>
<AnatomicalRegion>None</AnatomicalRegion>
<AppHost>http://singapore.blob.core.windows.net|</AppHost>
<CloudBlobBaseUri>blob.core.windows.net|</CloudBlobBaseUri>
<CloudComputeBaseUri>rdemo9.cloudapp.net|</CloudComputeBaseUr
i>
```

Annex 1

```
<CloudComputeDeployment>rdemo9</CloudComputeDeployment>
<CloudStorageAccount>singapore|</CloudStorageAccount>
<CloudTableBaseUri>table.core.windows.net|</CloudTableBaseUri
>
<ComputeHost>http://rdemo9.cloudapp.net/|</ComputeHost>
<ConfigHost>http://singapore.blob.core.windows.net/|</ConfigH
ost>
<Content>Image</Content>
<DZInstDataRelPath>/mysingapore/DicomImagesDLR_Head_Single/41
214342.dcm</DZInstDataRelPath>
<DZMHDDataRelPath>None</DZMHDDataRelPath>
<DZMetaDataRelPath>dicom</DZMetaDataRelPath>
<Drive>CLOUDDRIVE_VHD vhd/myvhdl.vhd</Drive>
<NameUC>-USECASE VRT -VOLUME_SWIZZLING false -MODE
DynamicLinearSampling -SHADING true</NameUC>
<ProcedureUid>mysingapore|</ProcedureUid>
<ServerBaseUri>http://singapore.blob.core.windows.net</Server
BaseUri>
<StorageFormat>DICOM</StorageFormat>
<StorageHost>http://singapore.blob.core.windows.net/|</Storag
eHost>
<StorageHostVolumeSeries2d>http://singapore.blob.core.windows
.net/mysingapore/IMAGES_POPIP/Data3D/RawVolumes/VRT_AngioCaro
tid_279/|</StorageHostVolumeSeries2d>
<StorageHostVolumeSeries2dAnz>1</StorageHostVolumeSeries2dAnz
>
<StorageType>LOCAL</StorageType>
<Thumb>http://singapore.blob.core.windows.net/mysingapore/thu
mbs/dlr.jpg</Thumb>
</Context>
```

Annex 2

```
<Context>
<PartitionKey xmlns =
"http://schemas.datacontract.org/2004/07/Microsoft.Samples.Wi
ndowsPhoneCloud.StorageClient"> GER</PartitionKey>
<RowKey xmlns =
"http://schemas.datacontract.org/2004/07/Microsoft.Samples.Wi
ndowsPhoneCloud.StorageClient">13acb1e8-ca04-4527-af73-
4f6ba492bb4d</RowKey>
<Timestamp xmlns =
"http://schemas.datacontract.org/2004/07/Microsoft.Samples.Wi
ndowsPhoneCloud.StorageClient">2012-02-
21T10:27:07.6956173Z</Timestamp>
<ARegion>Head</ARegion>
<AnatomicalRegion>None</AnatomicalRegion>
<AppHost>http://singapore.blob.core.windows.net/|</AppHost>
<CloudBlobBaseUri>blob.core.windows.net|</CloudBlobBaseUri>
<CloudComputeBaseUri>rdemo9.cloudapp.net|</CloudComputeBaseUr
i>
<CloudComputeDeployment>rdemo9|</CloudComputeDeployment>
<CloudStorageAccount>singapore|</CloudStorageAccount>
<CloudTableBaseUri>table.core.windows.net|</CloudTableBaseUri
>
<ComputeHost>http://rdemo9.cloudapp.net/|</ComputeHost>
<ConfigHost>http://singapore.blob.core.windows.net/|</ConfigH
ost>
<Content>Image</Content>
<DZInstDataRelPath>/mysingapore/DicomImagesDLR_Head_Single/41
214342.jpg</DZInstDataRelPath>
<DZMHDDataRelPath>None</DZMHDDataRelPath>
<DZMetaDataRelPath>jpg</DZMetaDataRelPath>
<Drive>CLOUDDRIVE_VHD vhd/myvhdl.vhd</Drive>
<NameUC>-USECASE VRT -VOLUME_SWIZZLING false -MODE
DynamicLinearSampling -SHADING true</NameUC>
<ProcedureUid>mysingapore|</ProcedureUid>
<ServerBaseUri>http://singapore.blob.core.windows.net</Server
BaseUri>
<StorageFormat>DICOMJPEG</StorageFormat>
<StorageHost>http://singapore.blob.core.windows.net/|</Storag
eHost>
<StorageHostVolumeSeries2d>http://singapore.blob.core.windows
.net/mysingapore/IMAGES_POPIP/Data3D/RawVolumes/VRT_Angio
Carotid_279/|</StorageHostVolumeSeries2d>
<StorageHostVolumeSeries2dAnz>1</StorageHostVolumeSeries2dAnz
>
<StorageType>LOCAL</StorageType>
<Thumb>http://singapore.blob.core.windows.net/mysingapore/thu
mbs/dlr.jpg</Thumb>
</Context>
```

Annex 3

```
<Context>
<PartitionKey xmlns =
"http://schemas.datacontract.org/2004/07/Microsoft.Samples.Wi
ndowsPhoneCloud.StorageClient"> GER</PartitionKey>
<RowKey xmlns =
"http://schemas.datacontract.org/2004/07/Microsoft.Samples.Wi
ndowsPhoneCloud.StorageClient">ti16 </RowKey>
<Timestamp xmlns =
"http://schemas.datacontract.org/2004/07/Microsoft.Samples.Wi
ndowsPhoneCloud.StorageClient">2012-02-
21T10:27:10.182866Z</Timestamp>
<ARegion>Head</ARegion>
<AnatomicalRegion>None</AnatomicalRegion>
<AppHost>http://singapore.blob.core.windows.net/|</AppHost>
<CloudBlobBaseUri>blob.core.windows.net</CloudBlobBaseUri>
<CloudComputeBaseUri>rdemo9.cloudapp.net|</CloudComputeBaseUr
i>
<CloudComputeDeployment>rdemo9|</CloudComputeDeployment>
<CloudStorageAccount>singapore|</CloudStorageAccount>
<CloudTableBaseUri>table.core.windows.net|</CloudTableBaseUri
>
<ComputeHost>http://rdemo9.cloudapp.net/|</ComputeHost>
<ConfigHost>http://singapore.blob.core.windows.net/|</ConfigH
ost>
<Content>image series</Content>
<DZInstDataRelPath>/mysingapore/DicomImagesDLR_Head/dcc_outpu
t.xml</DZInstDataRelPath>
```

Annex 3

```
<DZMHDDataRelPath>None</DZMHDDataRelPath>
<DZMetaDataRelPath>/mysingapore/GeneratedImages/Metadata.xml</DZMetaDataRelPath>
<Drive>None</Drive>
<NameUC>None</NameUC>
    <ProcedureUid>mysingapore|</ProcedureUid>
<ServerBaseUri>Cloud=blob.core.windows.net|TenantStorage=singapore|TenantCompute=rdemo9|Procedure=mysingapore|AppHost = http://singapore.blob.core.windows.net/|ConfigHost=http://singapore.blob.core.windows.net/|ComputeHost = http://rdemo9.cloudapp.net/|StorageHost = http://singapore.blob.core.windows.net|StorageHostVolumeSeries2d = http://singapore.blob.core.windows.net/mysingapore/IMAGES_POPIP/Data3D/RawVolumes/ct_600/|StorageHostVolumeSeries2dAnz=600</ServerBaseUri>
<StorageFormat>DICOM</StorageFormat>
<StorageHost>http://singapore.blob.core.windows.net/|</StorageHost>
<StorageHostVolumeSeries2d>http://singapore.blob.core.windows.net/mysingapore/DicomImagesDLR_Head/dcc_output_images/|</StorageHostVolumeSeries2d>
<StorageHostVolumeSeries2dAnz>4</StorageHostVolumeSeries2dAnz>
<StorageType>None</StorageType>
<Thumb>http://singapore.blob.core.windows.net/mysingapore/thumbs/dlr.jpg</Thumb>
</Context>
```

Annex 4

```
<Context>
<PartitionKey xmlns =
"http://schemas.datacontract.org/2004/07/Microsoft.Samples.WindowsPhoneCloud.StorageClient"> GER</PartitionKey>
<RowKey xmlns =
"http://schemas.datacontract.org/2004/07/Microsoft.Samples.WindowsPhoneCloud.StorageClient">ti16 </RowKey>
<Timestamp xmlns =
"http://schemas.datacontract.org/2004/07/Microsoft.Samples.WindowsPhoneCloud.StorageClient">2012-02-21T10:27:10.182866Z</Timestamp>
```

Annex 4

```
<ARegion>Head</ARegion>
<AnatomicalRegion>None</AnatomicalRegion>
<AppHost>http://singapore.blob.core.windows.net/|</AppHost>
<CloudBlobBaseUri>blob.core.windows.net|</CloudBlobBaseUri>
<CloudComputeBaseUri>rdemo9.cloudapp.net|</CloudComputeBaseUri>
<CloudComputeDeployment>rdemo9|</CloudComputeDeployment>
<CloudStorageAccount>singapore|</CloudStorageAccount>
<CloudTableBaseUri>table.core.windows.net|</CloudTableBaseUri>
<ComputeHost>http://rdemo9.cloudapp.net/|</ComputeHost>
<ConfigHost>http://singapore.blob.core.windows.net/|</ConfigHost>
<Content>image series</Content>
<DZInstDataRelPath>/mysingapore/DicomImagesDLR_Head/dzc_output.xml</DZInstDataRelPath>
<DZMHDDataRelPath>None</DZMHDDataRelPath>
<DZMetaDataRelPath>/mysingapore/GeneratedImages/Metadata.xml</DZMetaDataRelPath>
<Drive>None</Drive>
<NameUC>None</NameUC>
<ProcedureUid>mysingapore|</ProcedureUid>
<ServerBaseUri>Cloud=blob.core.windows.net|TenantStorage=singapore|TenantCompute=rdemo9|Procedure=mysingapore|AppHost = http://singapore.blob.core.windows.net/|ConfigHost = http://singapore.blob.core.windows.net/|ComputeHost = http://rdemo9.cloudapp.net/|StorageHost=http://singapore.blob.core.windows.net|StorageHostVolumeSeries2d = http://singapore.blob.core.windows.net/mysingapore/IMAGES_POPIP/Data3D/RawVolumes/ct_600/|StorageHostVolumeSeries2dAnz=600</ServerBaseUri>
<StorageFormat>DICOMJPEG</StorageFormat>
<StorageHost>http://singapore.blob.core.windows.net/|</StorageHost>
<StorageHostVolumeSeries2d>http://singapore.blob.core.windows.net/mysingapore/DicomImagesDLR_Head/dcc_output_images/|</StorageHostVolumeSeries2d>
<StorageHostVolumeSeries2dAnz>4</StorageHostVolumeSeries2dAnz>
<StorageType>None</StorageType>
<Thumb>http://singapore.blob.core.windows.net/mysingapore/thumbs/dlr.jpg</Thumb>
</Context>
```

Annex 5

```
<?xml version="1.0" encoding="utf-8"?>
<Collection MaxLevel="8" TileSize="256" Format="dcm"
NextItemId="65" ServerFormat=" Default"
xmlns="http://schemas.microsoft.com/deepzoom/2009">
    <Items>
        <I Id="0" N="0"
Source="dcc_output_images/1.3.12.2.1107.5.8.2.485257.835054.68674855.20080115074748630.dcm">
        <Size Width="512" Height="512" />
        <Viewport Width="1" X="-0" Y="-0" />
        </I>
        <I Id="1" N="1"
Source="dcc_output_images/1.3.12.2.1107.5.8.2.485257.835054.68674855.20080115074748840.dcm">
        <Size Width="512" Height="512" />
            <Viewport Width="1" X="-1" Y="-1" />
            ...
            <I Id="63" N="63"
                Source="dcc_output_images/1.3.12.2.1107.5.8.2.485257.835054.68674855.20080115074804300.dcm">
            <Size Width="512" Height="512" />
            <Viewport Width="1" X="-1" Y="-1" />
        </I>
        <I Id="64" N="64"
Source="dcc_output_images/1.3.12.2.1107.5.8.2.485257.835054.68674855.220080115074804550.dcm">
```

Annex 5

```
            <Size Width="512" Height="512" />
            <Viewport Width="1" X="-1" Y="-1" />
        </I>
    </Items>
</Collection>
```

Annex 6

```
<?xml version="1.0" encoding="utf-8" ?>
<Collection MaxLevel="8" TileSize="256" Format="jpg"
NextItemId="65" ServerFormat=" Default"
xmlns="http://schemas.microsoft.com/deepzoom/2009">
    <Items>
        <I Id="0" N="0"
        Source="dzc_output_images/1.3.12.2.1107.5.8.2.485257.835054
        .68674855.20080115074748630.jpg">
            <Size Width="512" Height="512" />
            <Viewport Width="1" X="-0" Y="-0" />
        </I>
        <I Id="1" N="1"
        Source="dzc_output_images/1.3.12.2.1107.5.8.2.485257.835054
        .68674855.20080115074748840.jpg" >
            <Size Width="512" Height="512" />
            <Viewport Width="1" X="-1" Y="-" />
        </I>
        ...
        <I Id="63" N="63"
        Source="dzc_output_images/1.3.12.2.1107.5.8.2.485257.835054
        .68674855.20080115074804300.jpg">
            <Size Width="512" Height="512" />
            <Viewport Width="1" X="-1" Y="-1" />
        </I>
        <I Id="64" N="64"
        Source="dzc_output_images/1.3.12.2.1107.5.8.2.485257.835054
        .68674855.220080115074804550.jpg">
            <Size Width="512" Height="512" />
            <Viewport Width="1" X="-1" Y="-1" />
        </I>
    </Items>
</Collection>
```

Annex 7

```
DcmApp.prototype.load_url = function(url, index, file_count) {
    var xhr = new XMLHttpRequest( );
    xhr.open('GET', url, true);
    xhr.responseType = 'arraybuffer';
    xhr.onload = (function(app) {
        return function(evt) {
            return app.load_arraybuffer(evt.target.response, index,
                    file_count, url);
        }
    }) (this);
    xhr.send( );
}
DcmApp.prototype.load_arraybuffer = function(abuf, index,
file_count, fileOrUrl) {
    var tcanvasuri;
    var app = this;
    var buffer = new Uint8Array(abuf);
    parser = new DicomParser(buffer);
    var file = parser.parse_file( );
    if (file == undefined) {
        app.files[index] = undefined;
        return;
    }
    if (file.Modality == "CT" file.Modality == "PT" ||
    file.Modality == "MR") {
        imageOrientation = file.ImageOrientationPatient;
        file.imageOrientationRow = imageOrientation.slice(0, 3);
        file.imageOrientationColumn = imageOrientation.slice(3, 6);
        app.organize_file(file);
    } else if(file.modality == "US") {
        file.RescaleIntercept = 0;
        file.RescaleSlope = 1;
        app.files[index] = file;
        app.organize_file(file);
    } else {
        file.RescaleIntercept = 0;
        file.RescaleSlope = 1;
        app.organize_file(file);
        app.files[index] = file;
    }
    app.curr_file_idx = index;
    if (file.PixelSpacing ! == undefined) {
        app.curr_series_uid = file.SOPInstanceUID;
        app.files[index] = file;
    }
    else {
        app.curr_series_uid = file.SeriesInstanceUID;
        app.files = app.series[app.curr_series_uid].files;
    }
    if (app.externalApp == true) {
        // do not draw in main canvas
    }
```

Annex 7

```
        else {
            app.draw_image( );
    }
        ++app.files_loaded;
    if (app.externalApp == true) {
        if(app.files_loaded == 1) {
            app.draw_image( );
        }
        fill_thumbnail(file.Columns, file.Rows,
            app.curr_series_uid, index, this, this.series,
            this.curr_series_uid, function (cid) { return new
            CanvasPainter(cid) });
        if(app.files_upload_enabled == true && dicom_Jpegflag ==
            false) {
            upload_DicomAsJpegImageWithCloudPath(fileOrUrl,
                file.Columns, file.Rows, app.curr_series_uid, index,
                app.files_loaded, file_count, this, this.series,
                this.curr_series_uid, function(cid) { return new
                    CanvasPainter(cid) });
        }
    }
    if(app.files_loaded == file_count) {
        if (file.PixelSpacing ! == undefined) {
        instance_number_sort(app.files);
        }
    }
}
```

Annex 8

```
function upload_DicomAsJpegImageWithCloudPath(srcpath, w, h,
uid, ind, loaded, totalCount, app, series, selected_uid,
painter_factory)
{
    var host = "blob.core.windows.net"; // microsoft azure
        storage
    var subscription = "singapore";
    var images_container = "mysingapore";
    var config_container = "config";
    var uploads_container = "uploads";
    var images_container_path = "http://" + subscription + "." +
        host + "/" + images_container;
    var config_container_path = "http://" + subscription + "." +
        host + "/" + config_container;
    var uploads_container_path = "http://" + subscription + "." +
        host + "/" + uploads_container;
    var images_container_cert = "?sr=c&si=kalle&sig=xxx";
    var config_container_cert = "?sr=c&si=kalle&sig=yyy";
    var uploads_container_cert = "?sr=c&si=kalle&sig=zzz";
    var srcSubPath = "dcc_output_images";
    var dstSubPath = "dzc_output_images";
    var dstpath1;
    if (totalCount > 1)
        dstpath1 = srcpath.replace(srcSubPath, dstSubPath);
    else
        dstpath1 = srcpath;
    var dstpath = dstpath1.replace(".dcm" ,".jpg");
    var pathend = srcpath.indexOf("dcc_output_images/")
    var cloudPathScenegraphXmlFile;
    if (totalCount > 1)
        cloudPathScenegraphXmlFile = srcpath.substring(0, pathend)
            + "dzc_output.xml";
    else
        cloudPathScenegraphXmlFile = "";
    var cloudPathTweetXmlFile = dicom_tweet_url;
    var upload_canvas = document.createElement("canvas");
    upload_canvas.id = 'canvas_thumb_' + ind;
```

Annex 8

```
    upload_canvas.width = w;
    upload_canvas.height = h;
    var painters = [//function(cid) { return new GLPainter(cid);
}, function(cid) { return new CanvasPainter(cid); },];
    for(var i in painters) {
        var painter = painters[i](upload_canvas.id);
        try {
            break;
        } catch(e) {
            console.log(e);
        }
    }
    painter.init(upload_canvas.id);
    if (app.externalApp == true) {
        painter.set_canvas(upload_canvas);
    }
    painter.set_cluts(ClutManager.r('Plain'),
ClutManager.g('Plain'),ClutManager.b('Plain'));
    painter.set_file(series[uid].files[0]);
    var retv = getWindowingValuesFromDcmFile (app,
series[uid].files[0]);
    wl = retv[0] ;
    ww = retv[1];
    painter.set_windowing(wl, ww);
    painter.draw_image( ); // draw thumbnail of image into canvas
    if (app.externalApp == true) {
        var dataUrl = upload_canvas.toDataURL("image/jpeg");
        // 1) save as jpeg file
        saveAnyDataUriTypeIntoCloudPathWithCert (dataUrl,
        "DicomJpg", "jpg", images_container_cert, dstpath,
        uploadDicomAsJpgDone);
        if(loaded == totalCount) {
            var str = dicom_dcc_output_xml;
            str = str.replace(/\b(dicom)\b/g, "jpg");
            str = str.replace(/\b(.dcm)\b/g, ".jpg");
            str = str.replace(/\b(dcc_output_images)\b/g,
                "dzc_output_images");
            var dststr = str;
            var retpath;
            if (totalCount > 1)
            retpath = saveAnyXmlFileIntoCloudPathWithCert (dststr,
                    images_container_cert,
                    cloudPathScenegraphXmlFile);
            //
            // 2) upload into config container the modified tweet file
                    for DICOMJPEG
            //
            str = dicom_tweet_xml;
            if (totalCount > 1)
            str = str.replace(/\b(dcc_output_images)\b/g,
                    "dzc_output_images");
            else
            str = str.replace(/\b(.dcm)\b/g, ".jpg");
            str = str.replace(/\b(DICOM)\b/g, "DICOMJPEG");
            //
            // Attention:
            // replace the path to jpeg, because if we want read in
                    pure DICOM later on we use the dcc_xxx
            //
            dststr = str;
            retpath =
            saveAnyXmlFileIntoCloudPathWithCertCb(dststr,
                    config_container_cert,
                    cloudPathTweetXmlFile,
                    uploadTweetAsXmlDone, dststr); // replace
                    tweet file
        }
    }
}
```

-continued

Annex 8

```
/* callback for DICOMJPEG Tweet xml file upload has been done
*/
function uploadTweetAsXmlDone (result, par) {
    if (result == true) {
        if (par != null) {
            //
            // 3) restart the app in same window with same url (but
            modified tweet content (DICOMJPEG))
            //
            doReloadInSameWindow( );
        }
    }
    else {
        // handle error here
        alert ("upload tweet error occurred: uri=" + par + " not
        successfully done!");
    }
}
/* callback for DICOMJPEG image upload has been done */
function uploadDicomAsJpgDone (result, par) {
    if (result == true) {
        if (par != null) {
            //alert ( "upload of uri=" + par + "
            successfully
done!");
        }
    }
    else {
        // handle error here
        alert ("upload error occurred: uri=" + par + " not
successfully done!");
    }
}
```

LIST OF REFERENCE SYMBOLS

1 Device
2 Internet
3 Cloud
4 Program code
5 Storage medium
6 Control instructions
7 Image data
8 Image data
9 User
B Image
i Index
S Special instruction
S1 to S45 Steps
ZA Access request
ZP Access path

What is claimed is:

1. A method for accessing image data stored in a cloud, the method being carried out by a device, the method comprising:
  transmitting, by the device, a request to the cloud to access the image data;
  receiving, at the device, an access path to the image data from the cloud;
  determining, by the device, whether the image data is in a first data format or in a second data format; and
  when the image data are in the first data format, then
    reading, by the device, the image data from the cloud via the access path;
    converting, by the device, the image data inside the device into the second data format;
    uploading, by the device, the image data converted into the second data format from the device to the cloud;
  modifying, by the device, the access path according to a modification rule, with a result that the access path is usable to discern that the image data are stored in the cloud in the second data format; and
  storing, by the device, the modified access path to the cloud.

2. The method of claim 1, wherein the modification of the access path comprises:
  at least one of changing a folder in which the image data are stored in the cloud and modifying a file type from an extension which characterizes the first data format to an extension which characterizes the second data format.

3. The method of claim 2, further comprising:
  deleting the image data stored in the first data format from the cloud, if the image data read, via the modified access path, from the cloud is in the second data format and matches prior image data read, via the access path, from the cloud in the first data format.

4. A non-transitory computer readable medium storing machine-readable program code for a device, the program code including control instructions, the execution of which causes the device to carry out the method of claim 2.

5. A non-transitory computer readable medium comprising program code segments which, when executed by a computer device, cause the computer device to perform the method of claim 2.

6. The method of claim 1, further comprising:
  storing, in the cloud, the image data in the first data format and an access path to the image data, before transmitting the request to access the image data to the cloud.

7. The method of claim 6, further comprising:
  deleting the image data stored from the first data format in the cloud, if the image data read, via the modified access path, from the cloud is in the second data format and matches prior image data read, via the access path, from the cloud in the first data format.

8. A non-transitory computer readable medium storing machine-readable program code for a device, the program code including control instructions, the execution of which causes the device to carry out the method of claim 6.

9. A non-transitory computer readable medium comprising program code segments which, when executed by a computer device, cause the computer device to perform the method of claim 6.

10. The method of claim 1, further comprising:
  deleting the image data stored in the first data format from the cloud, if the image data read, via the modified access path, from the cloud is in the second data format and matches prior image data read, via the access path, from the cloud in the first data format.

11. The method of claim 1, wherein the access method is carried out in a manner embedded in a web browser.

12. The method of claim 1, wherein
  the first data format is a Digital Imaging and Communications in Medicine (DICOM) format, and
  the second data format is a Joint Photographic Experts Group (JPEG) format or a Portable Network Graphics (PNG) format.

13. A non-transitory computer readable medium storing machine-readable program code for a device, the program code including control instructions, execution of which causes the device to carry out the method of claim 1.

14. A non-transitory computer readable medium comprising program code segments which, when executed by a computer device, cause the computer device to perform the method of claim 1.

15. The method of claim 1, wherein the converting includes retaining a local image resolution when converting the image data between the first data format and the second data format.

16. The method of claim 1, further comprising:
transmitting, by the device, a second request to the cloud to access the image;
receiving, at the device, a second access path to the image data from the cloud;
determining, by the device, whether the image data is in the first data format or in the second data format; and
when the image data are in the second data format, then
determining whether a special instruction is defined for the device,
reading the image data in the second data format from the cloud via the access path, if the special instruction is not defined for the device, the special instruction forcing the device to read the image data in the first data format irrespective of whether the image data is in the second data format, and
remodifying the second access path using a modification rule and reading the image data in the first data format from the cloud via the remodified access path, if the special instruction is defined for the device.

17. A device comprising:
a processor configured to access image data stored in a cloud by,
transmitting, by the device, a request to the cloud to access the image data,
receiving, by the device, an access path to the image data from the cloud,
determining, by the device, whether the image data is in a first data format or in a second data format; and
when the image data are in the first data format, then
reading, by the device, the image data from the cloud via the access path,
converting, by the device, the image data inside the device into the second data format,
uploading, by the device, the image data converted into the second data format from the device to the cloud,
modifying, by the device, the access path according to a modification rule, with a result that the access path is usable to discern that the image data are stored in the cloud in the second data format, and
storing, by the device, the modified access path in the cloud.

* * * * *